US010908681B2

(12) United States Patent
Meglan

(10) Patent No.: US 10,908,681 B2
(45) Date of Patent: Feb. 2, 2021

(54) OPERATING ROOM AND SURGICAL SITE AWARENESS

(71) Applicant: Covidien LP, Mansfield, MA (US)

(72) Inventor: Dwight Meglan, Westwood, MA (US)

(73) Assignee: COVIDIEN LP, Mansfield, MA (US)

(*) Notice: Subject to any disclaimer, the term of this patent is extended or adjusted under 35 U.S.C. 154(b) by 0 days.

(21) Appl. No.: 15/548,906

(22) PCT Filed: Jan. 22, 2016

(86) PCT No.: PCT/US2016/014419
§ 371 (c)(1),
(2) Date: Aug. 4, 2017

(87) PCT Pub. No.: WO2016/133644
PCT Pub. Date: Aug. 25, 2016

(65) Prior Publication Data
US 2018/0032130 A1  Feb. 1, 2018

Related U.S. Application Data

(60) Provisional application No. 62/118,841, filed on Feb. 20, 2015.

(51) Int. Cl.
G06F 3/01 (2006.01)
G02B 27/01 (2006.01)
(Continued)

(52) U.S. Cl.
CPC .............. *G06F 3/013* (2013.01); *A61B 34/25* (2016.02); *A61B 90/361* (2016.02);
(Continued)

(58) Field of Classification Search
CPC .......... G06F 3/013; G06F 3/012; G06F 3/017; G06F 3/011
See application file for complete search history.

(56) References Cited

U.S. PATENT DOCUMENTS 5,558,619 A * 9/1996 Kami ................. A61B 1/00006
600/106
5,836,869 A * 11/1998 Kudo ................. A61B 1/00039
600/173
(Continued)

FOREIGN PATENT DOCUMENTS

JP  2000231625 A  8/2000
JP  2001104331 A  4/2001
(Continued)

OTHER PUBLICATIONS

International Search Report for (PCT/US2016/014419) date of completion is Apr. 18, 2016 (3 pages).
(Continued)

*Primary Examiner* — Olga V Merkoulova
(74) *Attorney, Agent, or Firm* — Carter, DeLuca & Farrell LLP

(57) ABSTRACT

The present disclosure is directed to an augmented reality head mounted device worn by a user. The device includes an image capture device configured to capture an image of a surgical environment and a transparent lens configured to display an augmented image based on the image of the surgical environment. An eye tracking module coupled to the transparent lens configured to determine a direction of a gaze of an eye of the user, wherein the direction of the gaze of the eye determined by the eye tracking module is used to manipulate the augmented image.

17 Claims, 7 Drawing Sheets

(51) Int. Cl.

| | |
|---|---|
| *A61B 34/00* | (2016.01) |
| *G02B 27/00* | (2006.01) |
| *A61B 90/00* | (2016.01) |
| *G06F 3/16* | (2006.01) |
| *A61B 34/30* | (2016.01) |
| *A61B 17/00* | (2006.01) |
| *A61B 90/50* | (2016.01) |
| *A61B 1/04* | (2006.01) |

(52) U.S. Cl.
CPC ....... *G02B 27/0093* (2013.01); *G02B 27/017* (2013.01); *G06F 3/011* (2013.01); *G06F 3/017* (2013.01); *G06F 3/167* (2013.01); *A61B 1/041* (2013.01); *A61B 34/30* (2016.02); *A61B 2017/00203* (2013.01); *A61B 2017/00207* (2013.01); *A61B 2017/00216* (2013.01); *A61B 2090/365* (2016.02); *A61B 2090/502* (2016.02); *G02B 2027/014* (2013.01); *G02B 2027/0138* (2013.01); *G02B 2027/0187* (2013.01)

(56) References Cited

U.S. PATENT DOCUMENTS

| | | | |
|---|---|---|---|
| 9,767,608 B2* | 9/2017 | Lee | G06T 19/006 |
| 10,134,185 B2* | 11/2018 | Kihara | A61B 8/462 |
| 10,527,848 B2* | 1/2020 | Nakamura | G06F 3/011 |
| 2002/0082498 A1 | 6/2002 | Wendt et al. | |
| 2005/0206583 A1 | 9/2005 | Lemelson et al. | |
| 2007/0238981 A1* | 10/2007 | Zhu | A61B 90/36 |
| | | | 600/424 |
| 2011/0234484 A1* | 9/2011 | Ogawa | A61B 1/00039 |
| | | | 345/156 |
| 2013/0021374 A1* | 1/2013 | Miao | G06F 3/011 |
| | | | 345/633 |
| 2013/0169560 A1 | 7/2013 | Cederlund et al. | |
| 2013/0267838 A1* | 10/2013 | Fronk | A61B 5/066 |
| | | | 600/424 |
| 2013/0342572 A1 | 12/2013 | Poulos et al. | |
| 2014/0275760 A1* | 9/2014 | Lee | A61B 1/00045 |
| | | | 600/102 |
| 2015/0099946 A1* | 4/2015 | Sahin | A61B 5/16 |
| | | | 600/301 |
| 2015/0223731 A1* | 8/2015 | Sahin | A61B 5/16 |
| | | | 600/301 |
| 2015/0363979 A1* | 12/2015 | Takano | A61B 6/461 |
| | | | 345/633 |
| 2016/0026253 A1* | 1/2016 | Bradski | G02B 27/225 |
| | | | 345/8 |

FOREIGN PATENT DOCUMENTS

| | | |
|---|---|---|
| JP | 2004538538 A | 12/2004 |
| JP | 2006102495 A | 4/2006 |
| JP | 2011237987 A | 11/2011 |
| JP | 2013510673 | 3/2013 |
| JP | 2014155207 A | 8/2014 |
| JP | 2015019678 A | 2/2015 |
| WO | 2014103193 A1 | 7/2014 |
| WO | 2014125789 A1 | 8/2014 |
| WO | WO 2014-145166 | 9/2014 |

OTHER PUBLICATIONS

Extended European Search Report corresponding to counterpart Patent Application EP 16752773.8 dated Nov. 27, 2018.
Chinese First Office dated Aug. 15, 2019 corresponding to counterpart Patent Application CN 201680010428.1.
Japanese Notice of Allowance for application No. 2017-542077 dated May 18, 2020 with English translation.
Chinese Office Action for Application No. 201680010428.1 dated May 6, 2020 with English translation.

* cited by examiner

OPERATING ROOM AND SURGICAL SITE AWARENESS

CROSS-REFERENCE TO RELATED APPLICATIONS

This application is a U.S. National Stage application filed under 35 U.S.C. § 371(a) of International Patent Application No. PCT/US2016/014419, filed Jan. 22, 2016, which claims the benefit of and priority to U.S. Provisional Patent Application No. 62/118,841, filed Feb. 20, 2015, the entire disclosure of which is incorporated by reference herein.

BACKGROUND

Minimally invasive surgeries (MIS) have involved the use of multiple small incisions to perform a surgical procedure instead of one larger opening. The small incisions have reduced patient discomfort and improved recovery times. The small incisions have also limited the visibility of internal organs, tissue, and other matter.

A surgeon and the associated staff in a typical operating room communicate during MIS or robotic surgeries through non-optimal means. The surgeon's hands are often occupied with surgical tools or console controls which he/she cannot readily release to point out something that he/she needs or wants the operating room (OR) staff to observe and/or intervene/assist with. Verbal communication is used when possible (which can be difficult in the case of current robotic surgery systems) but this is not an information rich means of indicating a specific location on a patient, on an endoscope display, in the OR, and so on. In addition, during MIS and robotic surgeries, where the surgical field is typical only what is observed by an endoscope, things happening outside of that field of view are unknown which can lead to unobserved instrument collisions with anatomy, other instruments, and the like.

There is a need for improving communication between all the members involved with a surgical operation in order to improve patient outcome and increase efficiency and safety of a surgical procedure.

SUMMARY

In an aspect of the present disclosure, an augmented reality head mounted device worn by a user includes an image capture device configured to capture an image of a surgical environment and a lens configured to display an augmented image based on the image of the surgical environment. An eye tracking module is coupled to the lens and configured to determine a direction of a gaze of an eye of the user, wherein the direction of the gaze of the eye determined by the eye tracking module is used to manipulate the augmented image.

The augmented reality head mounted device may also include a microphone allowing the clinician to use voice commands.

The image capture device may capture three dimensional images in standard definition, high definition, or ultra-high definition formats.

The augmented image may include biometric data of a patient. The augmented image may also include a highlighted portion, wherein the highlighted portion is determined by the gaze of the eye of the user.

The lens may be transparent in some embodiments. In other embodiments, the image capture device may be mounted to a first side of the lens and a monitor may be mounted to a second side of the lens opposite the first side.

In another aspect of the present disclosure, a surgical system includes a surgical instrument, a first augmented reality head mounted display configured to be worn by a first user, and a second augmented reality head mounted display configured to be worn by a second user. The system also includes a controller configured to provide a first augmented image to the first augmented reality head mounted display and a second augmented image to the second augmented reality head mounted display.

In the surgical system the surgical instrument may be a robotic surgical instrument.

The surgical system may also include a surgical console including a robotic controller and a gesture detector. The gesture detector is configured to detect hand movement of the first user and provide a signal indicative of the hand movement to the controller. The first augmented image includes a virtual representation provided by the controller and the controller manipulates the virtual representation based on the signal. The virtual representation is an image of a patient or a virtual control panel.

The first augmented reality head mounted device includes a first image capture device configured to capture an image of a surgical environment and provide the first image to the controller, wherein the controller uses the first image to generate the first augmented image. The first augmented reality head mounted device also includes a first lens configured to receive and display the first augmented image and a first eye tracking module coupled to the first lens and configured to determine a direction of a gaze of an eye of the first user. The direction of the gaze of the eye of the first user determined by the first eye tracking module is used to manipulate the first augmented image.

The second augmented reality head mounted device includes a second image capture device configured to capture an image of a surgical environment and provide the second image to the controller, wherein the controller uses the second image to generate the second augmented image. The second augmented reality head mounted device also includes a second lens configured to receive and display the second augmented image and a second eye tracking module coupled to the second lens and configured to determine a direction of a gaze of an eye of the second user. The direction of the gaze of the eye of the second user determined by the second eye tracking module is used to manipulate the second augmented image.

In the surgical system the controller receives the gaze of the eye of the first user from the first tracking module, highlights a first portion of the first augmented image based on the gaze of the eye of the first user, and highlights a second portion of the second augmented image, wherein the second portion corresponds to the first portion.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
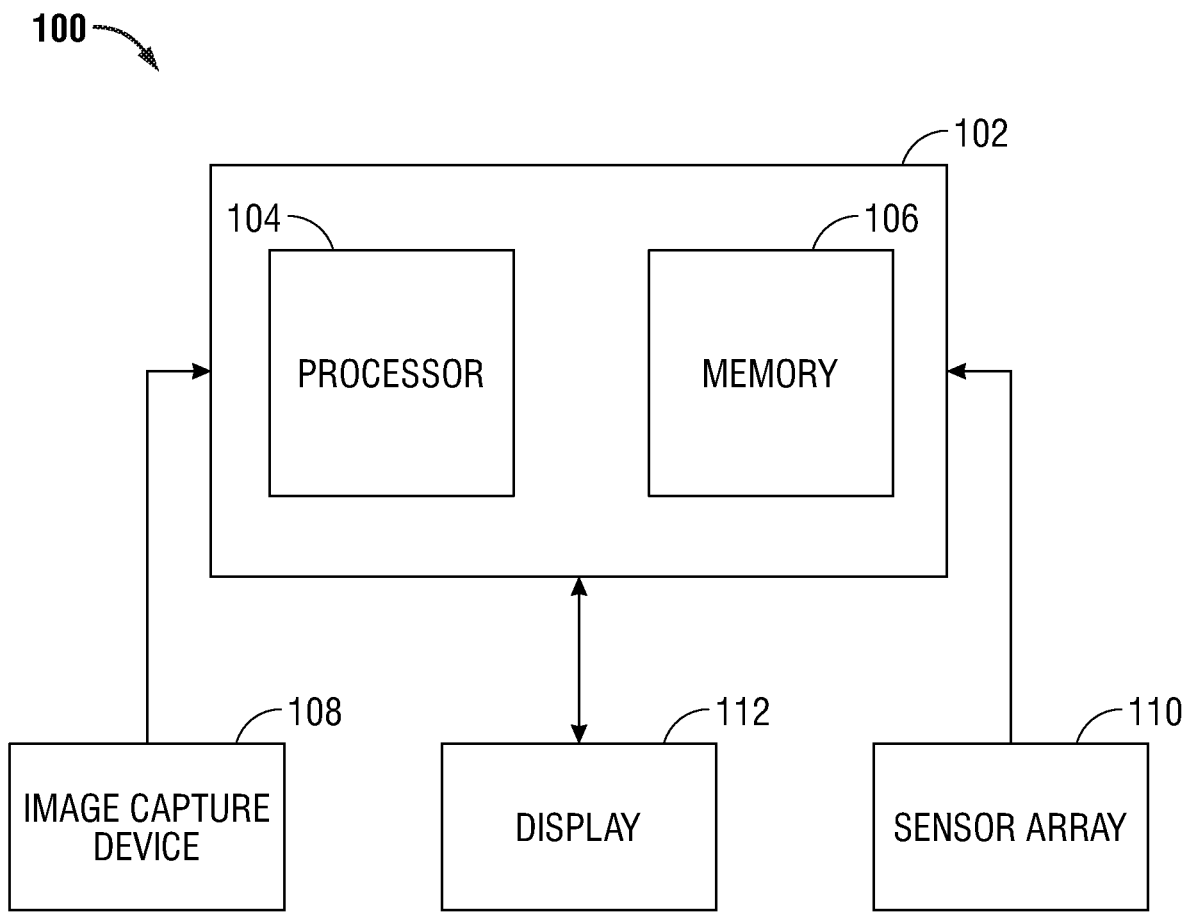
FIG. 1 is a block diagram of a system for augmenting a surgical environment in accordance with an embodiment of the present disclosure.

Image data captured from one or more surgical cameras during a surgical procedure may be presented to a clinician (e.g., a surgeon and/or operating room staff) via an augmented reality head mounted display (ARHMD). An ARHMD places a transparent surface between the clinician's eyes and the world around them. A small display reflects off of the transparent surface that is seen by the clinician at the same time that they see the world as well. The captured image data is interpreted by a computer to generate an augmented image that integrates appropriately with what the clinician sees to augment what they normally observe.

In order to further improve the surgical procedure, the ARHMD may include an eye tracker to monitor the clinician's gaze. By monitoring the clinician's gaze, the location of an item that the clinician is looking for may be determined and appropriately marked in the display of another person who is looking at the same location but from a different point of view. Eye tracking may also be combined with voice recognition or other forms of non-hand centric intention indication (e.g. a specific eye blink pattern), so that the clinician can look at an item, indicate that he/she wants someone else to be shown the same item, and the other person will see the item from their viewpoint.

Using the ARHMD and a computerized oversight system, the clinician may have their hand and finger movements monitored and the clinician may interact with virtual air-based controls (e.g., switches, dials, keyboards, etc.). As such, complex commands can be transferred to the computer oversight system without the need for sterile equipment.

In addition to the clinician being able to communicate spatially definite information to others also wearing ARHMDs, the computer oversight system can observe actions of the surgeon and/or staff as well as what is seen by the clinician and/or staff in the OR and can inject contextually appropriately information to their views. For example, if a surgeon indicates that a tool needs to be changed on a surgical robot. The OR staff could have an indicator automatically placed on the display of their respective ARHMDs showing where the new tool is located followed by indications as to where they need to place it for the tool change. This type of action sequence assistance display could be tailored to the context of the skill/experience of the surgeon and OR staff so that only the level of assistance/guidance appropriate to the room is provided.

Instrument ports may also be used with the ARHMD in either robotic or traditional MIS procedures. The ports would contain cameras, combined with computer vision software, capable of comprehending the spatial information of the surgical site seen by the cameras. The segmented and interpreted scene information would be derived from combining the camera data from all the ports to provide a comprehensive and constant understanding of the surgical site. Based on the combined camera data the oversight computer would have a comprehensive understanding of the surgical site beyond what the surgeon and/or OR staff would see through the endoscope view. This information would be used by the oversight system to determine things that the surgeon and/or OR staff could potentially find useful (e.g. tools colliding with anatomy outside the endoscope view) and could communicate this insight in a spatially correct manner by injecting appropriate imagery into the augmented image provided on the ARHMD of each person involved in the surgery.

In addition to the data coming from the cameras on the ARHMDs and the instrument ports, additional spatially aware cameras could be present in the OR (such as on robot arms or located on booms or on the ceiling above the OR table) which could also feed into the computer vision software providing it with a comprehensive overview of the OR table vicinity as well as the surgical site within the patient. In this way, a broad range of insights helpful to the surgeon and OR staff in carrying out efficacious, time and safety effective procedures can be appropriately made available through the ARHMDs.

In addition to the ARHMDs, projectors mounted around the OR table may be used to display the contents of the ARHMDS to individuals not wearing ARHMDs. These projectors would allow appropriate visual indicators to be overlaid on top of the physical entities in the OR table area as needed. By including 3D depth aware cameras with the projectors, the images projected could be adjusted to appear correctly to observers even when the images are shown on curved surfaces.

One or more of these technologies may be included as part of an imaging system in a surgical robotic system to provide a clinician with additional information in real time about unapparent conditions and objects within and/or outside of an endoscope's field of view.

The present disclosure is directed to systems and methods for providing an augmented image in real time to a clinician during a surgical procedure. The systems and methods described herein may use a combination of eye tracking, voice recognition, and/or hand-gestures to permit operating room staff to communicate effectively with other operating room staff.

The system of displays, interaction monitoring, and automatic intelligence distillation about ongoing surgical procedures described herein provides multiple benefits over the current situation for surgeons and OR staff working in MIS and robotic surgical procedures. The wearer of an ARHMD equipped with eye gaze tracking can show another person wearing an ARHMD exactly what they are interested in, in the OR or surgical site. This allows detailed communication of location centric information to be reliably transferred between the surgeon and OR staff which improves efficiency and safety.

This communication approach also allows location centric communication without requiring the participants to remove their hands from sterile devices, again improving surgical efficiency. The use of hand/gesture tracking/interpretation also allows commands to given to the surgical system without requiring additional sterility accommodations, again improving the efficiency of procedures. These commands can result in automated initiation of illustrative annotation of specific ARHMDs to coordinate actions such as tool changes on a surgical robot. The level of guidance being adjustable to the level of skill/experience of a specific team member enhances the efficiency and safety of a procedure.

Automatic understanding of tool actions at the surgical site and subsequent notification of the surgeon and/or OR staff of issues warranting attention will improve the efficiency and safety of surgery. For example, inadvertent tool-tissue contact can be avoided. Another benefit of automatic evaluation of the surgical site is that placed objects such as sponges can be noted and their removal checked at the end of a procedure, thereby increasing the safety of a procedure.

Turning to FIG. 1, a system for augmenting a surgical environment, according to embodiments of the present disclosure, is shown generally as 100. System 100 includes a controller 102 that has a processor 104 and a memory 106. Memory 106 stores oversight software that is executed by the processor 104. The system 100 also includes an image capture device 108, e.g., a camera, that records still frame images or moving images. One or more image captured devices 108 may be placed in one or more locations in the surgical environment including, but not limited to, above the operating table, on surgical tools, on various portions of a robotic surgical system, etc. A sensor array 110 provides information concerning the surgical environment to the controller 102. For instance, sensor array 110 includes biometric sensors capable of obtaining biometric data of a patient such as, pulse, temperature, blood pressure, blood oxygen levels, heart rhythm, etc. A display 112, displays augmented images to a clinician during a surgical procedure. In some embodiments, the controller 102 may communicate with a central server (not shown) via a wireless or wired connection. The central server may store images of a patient or multiple patients that may be obtained using x-ray, a computed tomography scan, or magnetic resonance imaging.

The images captured by the one or more image capture devices 108 are provided to the controller 102 to provide a comprehensive overview of a surgical environment which is provided to the display 112. The comprehensive overview may provide a broad range of insights to assist the one or more clinician in carrying out an efficient and safe surgical procedure.

Figure 2:
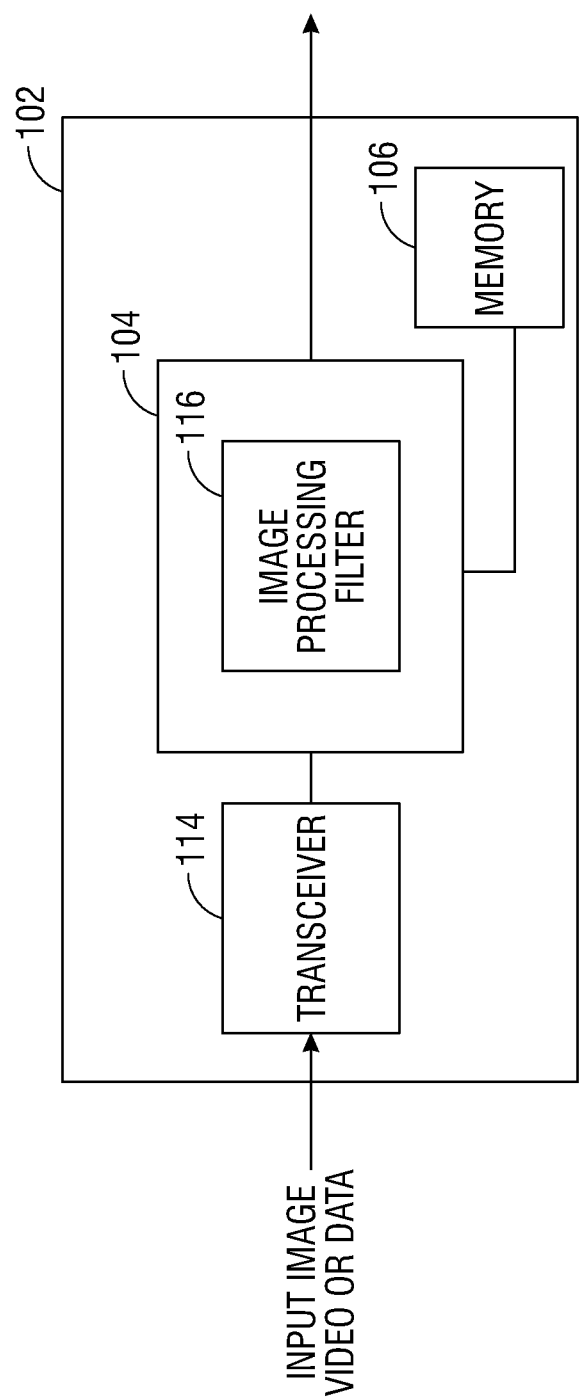
FIG. 2 is a system block diagram of the controller of FIG. 1.

FIG. 2 depicts a system block diagram of the controller 102. As shown in FIG. 2, the controller 102 includes a transceiver 114 configured to receive still frame images, video, or data. In some embodiments, the transceiver 114 may include an antenna to receive the still frame images, video, or data via a wireless communication protocol. The still frame images, video, or data are provided to the processor 104. The processor 104 includes an image processing filter 116 that processes the received still frame images, video, or data to generate an augmented image or video. The image processing filter 116 may be implemented using discrete components, software, or a combination thereof. The augmented image or video is provided to the display 112.

Figure 3:
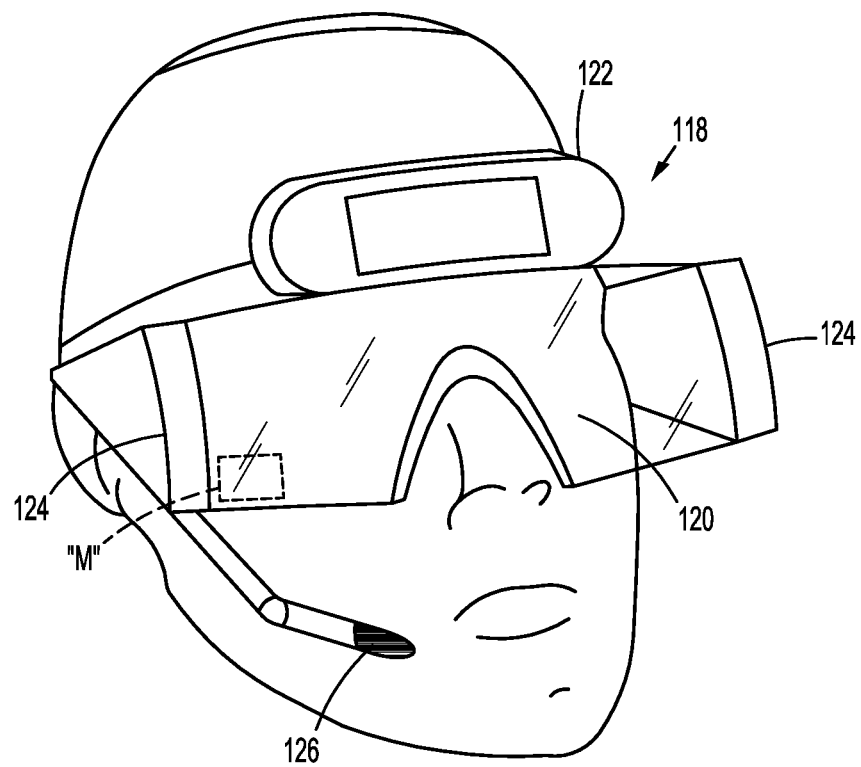
FIG. 3 is a perspective view of an augmented reality head mounted display in accordance with embodiments of the present disclosure.

FIG. 3 depicts an example of a display 112 in the form of an ARHMD 118. As shown in FIG. 3, the ARHMD 118 includes a transparent lens display 120 that, when worn, is positioned between the clinician's eyes and the surgical environment. The ARHMD 118 also includes an image capture device 122 capable of taking still or moving images in the surgical environment. Images captured by the image capture device 122 are interpreted by the controller 102 and augmented before being displayed on transparent lens display 120. The image capture device 122 may take three dimensional images in standard definition, high definition, and/or ultra-high definition. The three dimensional images are processed to form an augmented image allowing the clinician to perceive depth in the augmented image.

The ARHMD 118 also includes eye tracking modules 124 configured to track eye movement of the clinician wearing the ARHMD 118. Eye tracking modules 124 emit light that is reflected off of the eye and detected by a camera or any other optical sensors. The detected reflected light is analyzed by the controller 102 to extract eye rotation from changes in reflections. In some embodiments, the controller 102 may use corneal reflection and the center of the pupil as features to track over time. In other embodiments, reflections from the front of the cornea and the back of the lens are used to track eye movement. In yet other embodiments, features from inside the eye, e.g., the retinal blood vessels, are followed as the eye rotates. These methods of eye tracking are capable of tracking the gaze of the clinician so that the controller 102 may determine a location of interest for the clinician. The eye tracking module 124 is also capable of interpreting non-hand centric intention indications such as blink patterns.

The ARHMD 118 may also include a microphone 126 to receive voice commands from the clinician which will be described in more detail below.

Figure 4:
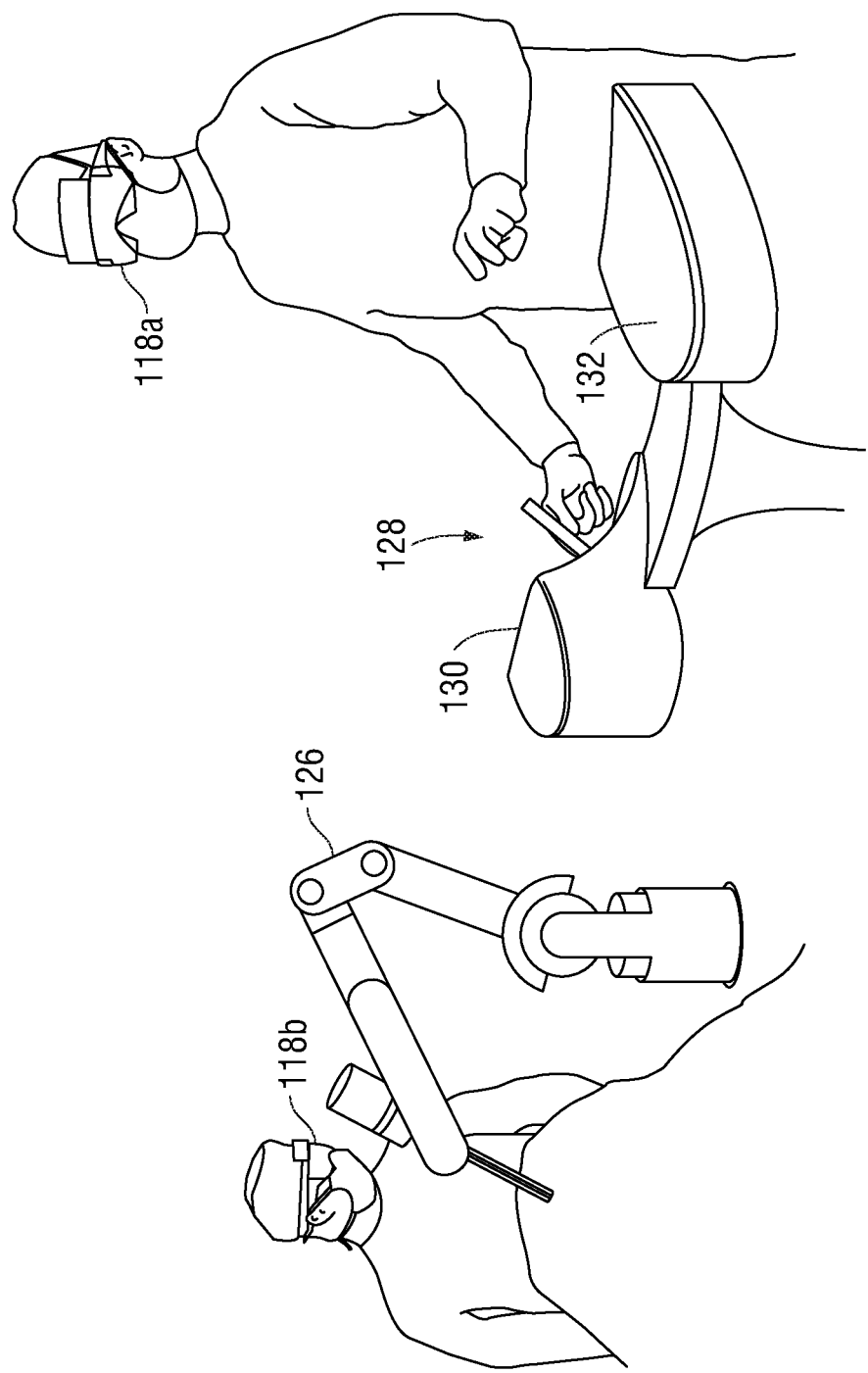
FIG. 4 is a representative diagram of a surgical environment.

FIG. 4 depicts a surgical environment that utilizes the embodiments described herein. As can be seen in FIG. 4, the surgical environment includes a surgeon wearing an ARHMD 118a and an operating room (OR) staff member wearing another ARHMD 118b. The surgeon operates a robotic surgical instrument 126 using a surgical console 128. Robotic surgical instrument 126 may be any known robotic surgical instrument. Surgical console 128 includes a robotic controller 130 configured to send commands to the robotic surgical instrument 126. Robotic controller 130 may transmit commands to the robotic surgical instrument 126 via any conventional methods.

The surgical console also includes a gesture detector 132 configured to detect a hand gesture of the clinician.

Figure 5:
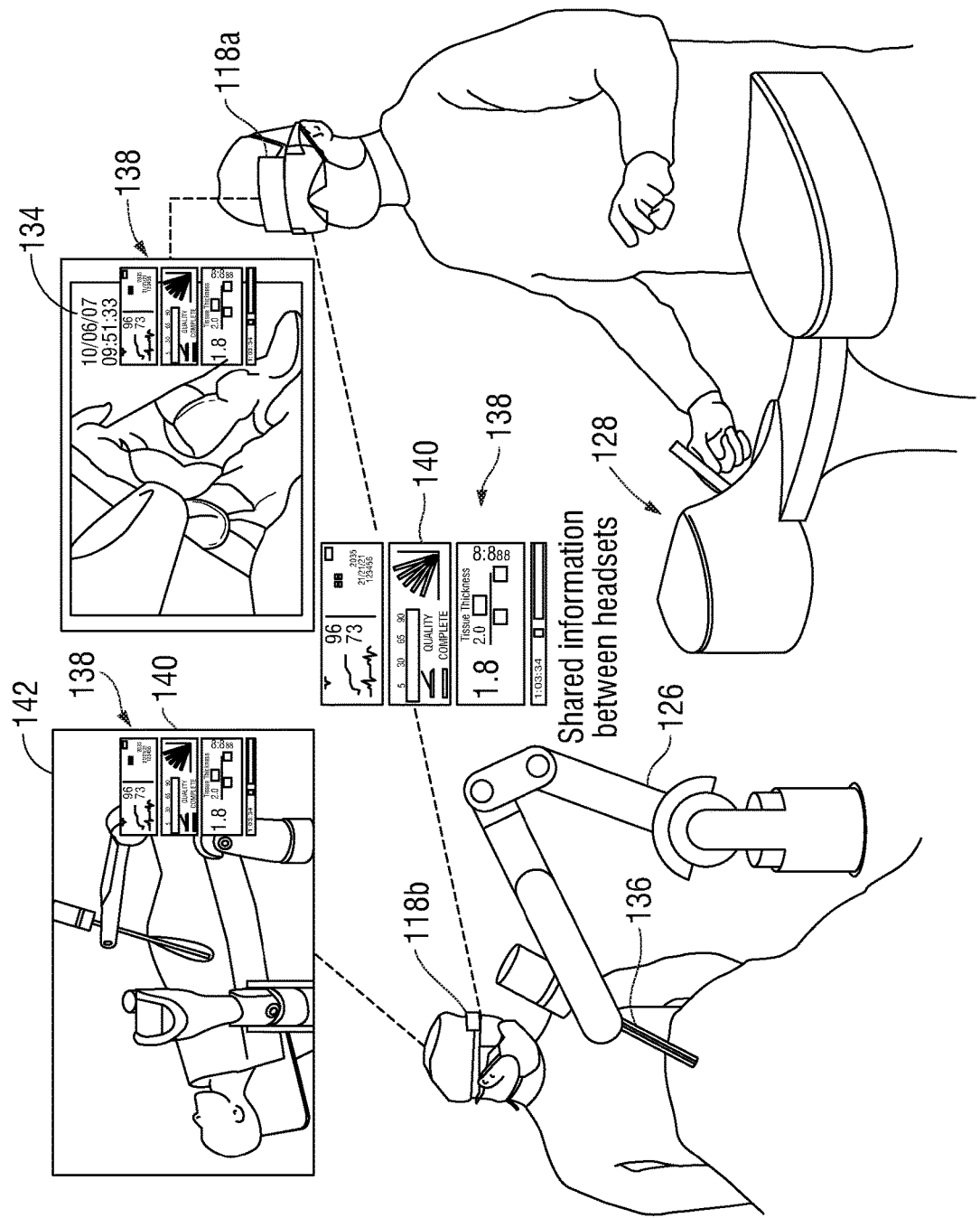
FIG. 5 is a representative diagram of a surgical environment including the images shown in the augmented reality head mounted display of FIG. 3.

FIG. 5 depicts a surgical environment including the images shown in ARHMDs 118a and 118b. As shown in FIG. 5, ARHMD 118a depicts an augmented image 134 of the patient taken by an image capture device (e.g., image capture device 108) disposed on surgical tool 136. In this example, image 134 is a laparoscopic view of a patient during a minimally invasive surgical procedure. During the procedure, the surgeon may realize that the surgical tool 136 needs to be replaced or a staple or clip cartridge may be depleted soon. For example, the eye tracking module 124 would track the surgeon's gaze to the screen 138, and in particular, the eye tracking module 124 would track the surgeon's gaze to portion 140 of screen 138 which indicates the tool status. Eye tracking module 124 would then transmit a signal to controller 102 which would highlight portion 140 in the augmented image and provide the augmented image with a highlighted portion 140 to both ARHMDs 118a and 118b. In the augmented image 142 shown on ARHMD 118b which displays an augmented image from the point of view of the person wearing the ARHMD 118b, the screen 138 would have a highlighted portion 140 indicating that the surgical tool 136 needs to be replaced or a staple or clip cartridge may be depleted soon. In some embodiments, image 142 would highlight an image 144 of the surgical tool 136 from the perspective of the OR staff member so that the OR staff member would be informed of the need to replace all or a part of the surgical tool 136. Because the surgeon who operates the robotic surgical instrument 126 is often in a non-sterile environment, using the ARHMD 118*a* allows the surgeon to easily communicate with the OR staff member and permit the OR staff member to realize that a new staple or clip cartridge or surgical tool may be needed.

In some embodiments, the surgeon may also look around the OR to search for a specific item. Once the surgeon's gaze settles on the item in the augmented image shown on ARHMD 118*a*, using a voice command, blink pattern, or any other form of commands, the ARMHD 118*b* of the OR staff member would highlight the item in the augmented image shown on ARMHD 118*b* from their individual perspective.

In other embodiments, the ARHMDs 118*a* and 118*b* may receive augmented images from the controller 102 that were derived from combining image data from all of the image capture devices 108 to provide a comprehensive and constant understanding of the surgical site. Based on the combined image data, the controller 102 would have a comprehensive understanding of the surgical site beyond what the surgeon and/or OR staff would see through the endoscope view. This information would be used by the controller 102 to determine things that the surgeon and/or OR staff could potentially find useful (e.g. tools colliding with anatomy outside the endoscope view) and could communicate this insight in a spatially correct manner in the augmented image provided on the ARHMD 118*a* or 118*b*.

Figure 6:
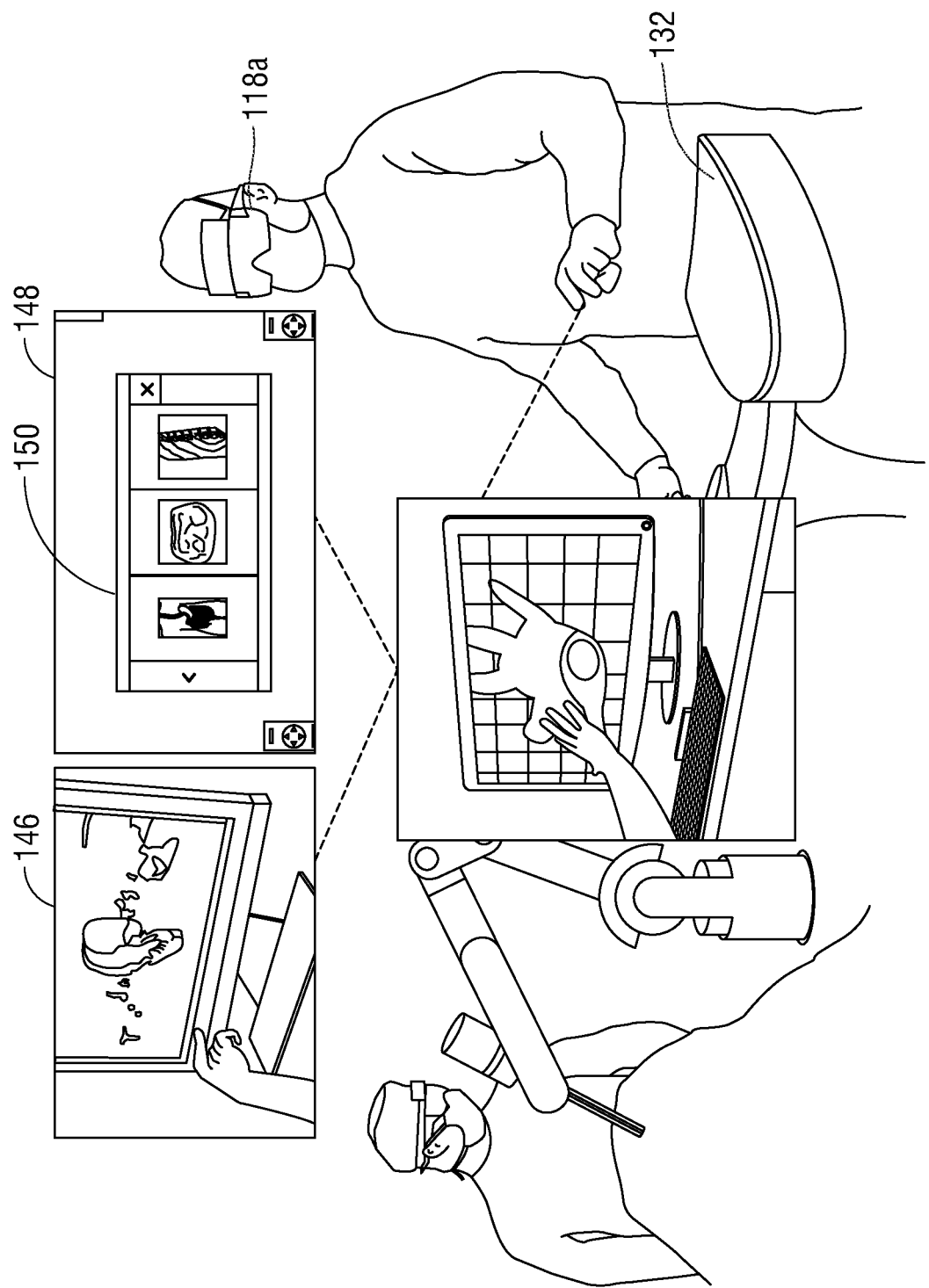
FIG. 6 is a representative diagram depicting gesture control of the images shown on the augmented reality head mounted display.

FIG. 6 depicts a surgical environment where hand and finger gestures are monitored to provide a more detailed interaction between the clinician wearing the ARHMD 118*a* and the controller 102. Controller 102 obtains an image 146 that was previously obtained, and displays a virtual representation 150 of image 146 in augmented image 148. The clinician views the virtual representation 150 on ARHMD 118*a* and using his hand and/or fingers, the clinician can manipulate the virtual representation 150. In particular, gesture detector 132 detects the hand and/or finger movement of the surgeon and transmits a signal indicative of such movement to controller 102. The controller 102 spatially resolves the detected hand and/or finger movement along with the virtual representation 150 to manipulate the virtual representation 150. For instance, the clinician can pinch his fingers to zoom in or separate his fingers to zoom out of an image. The clinician can point to a particular image in the virtual representation 150 to highlight the image.

In some embodiments, a virtual control panel may be shown on the ARHMD 118*a* so that the clinician can interact with virtual/air-based controls such as, but not limited to, switches or dials for an electrosurgical or electromechanical instrument or a virtual keyboard. Using virtual/air-based controls reduces the number of sterile equipment needed in an OR. As described above, gesture detector 132 would detect the hand and/or finger movement of the surgeon and transmit a signal indicative of such movement to controller 102. The controller 102 would spatially resolve the detected hand and/or finger movement along with the virtual/air-based controls to perform a command based on the clinician's hand and/or finger movement.

Figure 7:
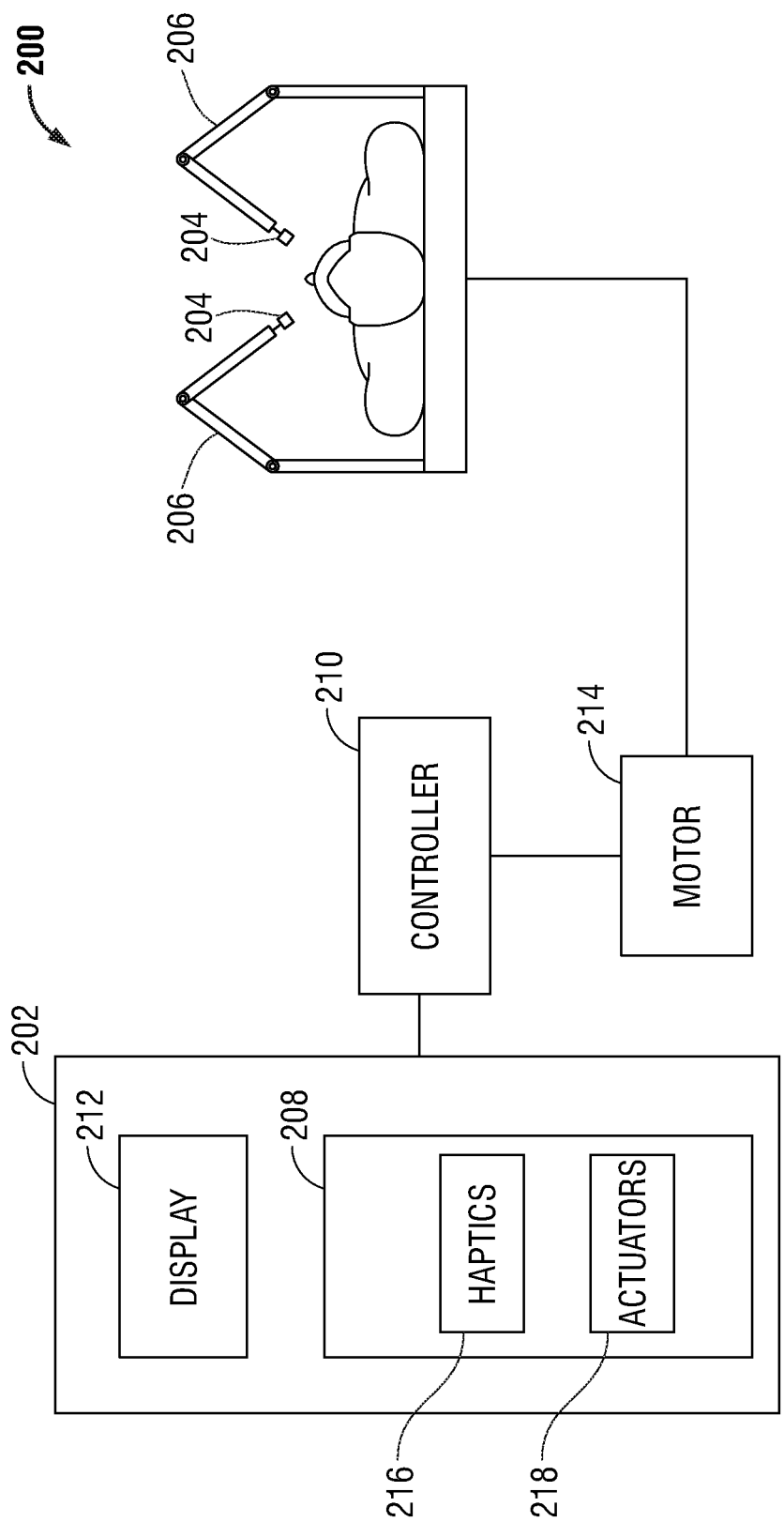
FIG. 7 is a system block diagram of a robotic surgical system in accordance with an embodiment of the present disclosure.

As shown in FIG. 7, a robotic surgical system 200 may be employed with one or more consoles 202 that are next to the operating theater or located in a remote location. In this instance, one team of clinicians or nurses may prep the patient for surgery and configure the robotic surgical system 200 with one or more instruments 204 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 206 of the surgical system 200 are typically coupled to a pair of master handles 208 by a controller 210. Controller 210 may be integrated with the console 202 or provided as a standalone device within the operating theater. The handles 206 can be moved by the clinician to produce a corresponding movement of the working ends of any type of surgical instrument 204 (e.g., probe, end effectors, graspers, knifes, scissors, etc.) attached to the robotic arms 206. For example, surgical instrument 204 may be a probe that includes an image capture device. The probe is inserted into a patient in order to capture an image of a region of interest inside the patient during a surgical procedure. One or more of the image processing filters 116 are applied to the captured image by the controller 210 before the image is displayed to the clinician on a display 212.

The movement of the master handles 208 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 204.

During operation of the surgical system 200, the master handles 208 are operated by a clinician to produce a corresponding movement of the robotic arms 206 and/or surgical instruments 204. The master handles 208 provide a signal to the controller 208 which then provides a corresponding signal to one or more drive motors 214. The one or more drive motors 214 are coupled to the robotic arms 206 in order to move the robotic arms 206 and/or surgical instruments 204.

The master handles 208 may include various haptics 216 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 216 provide the clinician with enhanced tactile feedback simulating actual operating conditions. The haptics 216 may include vibratory motors, electroacitve polymers, piezoelectric devices, electrostatic devices, subsonic audio wave surface actuation devices, reverse-electrovibration, or any other device capable of providing a tactile feedback to a user. The master handles 208 may also include a variety of different actuators 218 for delicate tissue manipulation or treatment further enhancing the clinician's ability to mimic actual operating conditions.

In the embodiments described herein, the ARHMD 118 includes a transparent lens display 120. However, ARHMDs that do not have a transparent display may also be used with the embodiments described herein. For example, the ARHMD may have one or more lenses with each lens including a camera attached to a front of the lens to capture an image of the surgical environment. Once the image undergoes one or more of the image processing techniques described herein, the processed or augmented image is displayed on a monitor "M"0 attached to the back of the lens that blocks the view of the user. Thus, the captured images may be manipulated before they are displayed to the user.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refers to a clinician or any medical professional, such as a doctor, nurse, technician, medical assistant, or the like) performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An augmented reality head mounted device worn by a first user comprising:
    an image capture device configured to capture a real time image of a surgical environment from a first point of view of the first user;
    a lens configured to display an augmented real time image based on the real time image of the surgical environment; and
    an eye tracking module coupled to the lens and configured to determine a direction of a gaze of an eye of the first user,
    wherein the eye tracking module is configured to:
        manipulate the augmented real time image based on the direction of the gaze of the eye of the first user from the first point of view;
        transmit the manipulated augmented real time image to another augmented reality head mounted device worn by a second user; and
        receive a manipulated augmented real time image from a direction of a gaze of an eye of the second user from a second point of view of the another augmented reality head mounted device worn by the second user.

2. The augmented reality head mounted device of claim 1, further comprising a microphone.

3. The augmented reality head mounted device of claim 1, wherein the image capture device captures a three dimensional image.

4. The augmented reality head mounted device of claim 1, wherein the augmented real time image includes biometric data of a patient.

5. The augmented reality head mounted device of claim 1, wherein the augmented real time image includes a highlighted portion, wherein the highlighted portion is determined by the gaze of the eye of the first user.

6. The augmented reality head mounted device of claim 1, wherein the lens is transparent.

7. The augmented reality head mounted device of claim 1, wherein the image capture device is mounted to a first side of the lens and a monitor is mounted to a second side of the lens opposite the first side.

8. A surgical system comprising:
    a surgical instrument;
    a first augmented reality head mounted display configured to be worn by a first user, and a second augmented reality head mounted display configured to be worn by a second user,
    wherein the first augmented reality head mounted display includes:
        an image capture device configured to capture a real time image of a surgical environment from a first point of view of the first user;
        a lens configured to display an augmented real time image based on the real time image of the surgical environment; and
        an eye tracking module coupled to the lens and configured to determine a direction of a gaze of an eye of the first user, wherein the eye tracking module of the first augmented reality head mounted display is configured to:
  manipulate the augmented real time image based on the direction of the gaze of the eye of the first user;
  transmit the manipulated augmented real time image to the second augmented reality head mounted device worn by the second user; and
  receive a manipulated augmented image from a second point of view of a second user wearing the second augmented reality head mounted device;
wherein the second augmented reality head mounted display includes:
  an image capture device configured to capture a real time image of the surgical environment from the second point of view of the second user;
  a lens configured to display the augmented real time image based on the real time image of the surgical environment; and
  an eye tracking module coupled to the lens and configured to determine a direction of a gaze of an eye of the second user, wherein the eye tracking module of the second augmented reality head mounted display is configured to:
    manipulate the real time augmented image based on the direction of the gaze of the eye of the second user;
    transmit the manipulated augmented real time image to the first augmented reality head mounted device worn by the first user; and
    receive a manipulated augmented image from the first point of view of the first user wearing the first augmented reality head mounted device; and
a controller configured to:
  generate the augmented real time image based on the real time image of the surgical environment by combining the real time image of the surgical environment from the point of view of the first user and the real time image of the surgical environment from the point of view of the second user;
  provide a first augmented real time image of the surgical environment to the first augmented reality head mounted display, generated from the augmented real time image, and corresponding to the point of view of the first user; and
  provide a second augmented real time image of the surgical environment to the second augmented reality head mounted display, generated from the augmented real time image, and corresponding to the point of view of the second user.

9. The surgical system of claim 8, wherein the surgical instrument is a robotic surgical instrument.

10. The surgical system of claim 9, further comprising a surgical console including a robotic controller and a gesture detector.

11. The surgical system of claim 10, wherein the gesture detector is configured to detect hand movement of the first user and provide a signal indicative of the hand movement to the controller.

12. The surgical system of claim 11, wherein the first augmented image includes a virtual representation provided by the controller and the controller manipulates the virtual representation based on the signal.

13. The surgical system of claim 12, wherein the virtual representation is an image of a patient.

14. The surgical system of claim 12, wherein the virtual representation is a virtual control panel.

15. The surgical system of claim 8, wherein the eye tracking module of the first augmented reality head mounted display is configured to determine a direction of a gaze of an eye of the first user,
  wherein the direction of the gaze of the eye of the first user determined by the eye tracking module of the first augmented reality head mounted display is used to manipulate the first augmented image.

16. The surgical system of claim 15, wherein the eye tracking module of the second augmented reality head mounted display is configured to determine a direction of a gaze of an eye of the second user,
  wherein the direction of the gaze of the eye of the second user determined by the eye tracking module of the second augmented reality head mounted display is used to manipulate the second augmented real time image.

17. The surgical system of claim 16, wherein the controller receives the direction of the gaze of the eye of the first user from the eye tracking module of the first augmented reality head mounted display, highlights a first portion of the first augmented real time image based on the direction of the gaze of the eye of the first user, and highlights a second portion of the second augmented real time image, wherein the second portion corresponds to the first portion.

* * * * *